United States Patent
Lehmann et al.

(10) Patent No.: US 6,172,823 B1
(45) Date of Patent: *Jan. 9, 2001

(54) MODE MATCHING FOR CAVITY RING-DOWN SPECTROSCOPY BASED UPON BREWSTER'S ANGLE PRISM RETROREFLECTORS

(75) Inventors: Kevin K. Lehmann, Lawrenceville; Paul Rabinowitz, Bridgewater, both of NJ (US)

(73) Assignee: Trustees of Princeton University, Princeton, NJ (US)

( * ) Notice: Under 35 U.S.C. 154(b), the term of this patent shall be extended for 0 days.

This patent is subject to a terminal disclaimer.

(21) Appl. No.: 09/488,353

(22) Filed: Jan. 20, 2000

Related U.S. Application Data

(63) Continuation-in-part of application No. 09/412,069, filed on Oct. 4, 1999, now Pat. No. 6,097,555, which is a continuation-in-part of application No. 08/955,126, filed on Oct. 21, 1997, now Pat. No. 5,973,864.

(51) Int. Cl.[7] .................. G02B 5/04; G01J 3/00; G01N 21/00; H01S 3/08
(52) U.S. Cl. ............ 359/834; 359/836; 359/837; 372/92; 372/93; 372/100; 372/94; 356/300; 356/436; 356/445
(58) Field of Search ................. 359/831, 833, 359/834, 835, 836, 837, 857, 858; 356/300, 436, 437, 438, 439, 445; 372/16, 72, 92, 93, 94, 95, 100

(56) References Cited

U.S. PATENT DOCUMENTS

| | | |
|---|---|---|
| 3,402,364 | 9/1968 | De Lang . |
| 3,711,788 | 1/1973 | Forkner . |
| 3,982,203 | 9/1976 | De Wit . |
| 4,161,436 | 7/1979 | Gould . |
| 4,525,034 | 6/1985 | Simmons . |
| 4,677,639 | 6/1987 | Sasser . |
| 4,740,986 | 4/1988 | Reeder . |
| 4,746,201 | 5/1988 | Gould . |
| 5,276,548 | 1/1994 | Margalith . |
| 5,463,493 | 10/1995 | Shah . |
| 5,483,342 | 1/1996 | Rockwell . |
| 5,528,040 | 6/1996 | Lehmann . |
| 5,835,231 | 11/1998 | Pipino . |
| 5,912,740 | 6/1999 | Zare et al. . |
| 5,973,864 | * 10/1999 | Lehmann et al. ............ 359/834 |
| 6,097,555 | * 8/2000 | Lehmann et al. ............ 359/834 |

FOREIGN PATENT DOCUMENTS 63-013386    1/1988   (JP) .

OTHER PUBLICATIONS

International Search Report dated Jan. 29, 1999.
J. White, Long Optical Paths of Large Aperture, 32 *J. Opt. Soc. Amer.*, 285 (May, 1942).

(List continued on next page.)

*Primary Examiner*—Ricky D. Shafer
(74) *Attorney, Agent, or Firm*—Ratner & Prestia

(57) ABSTRACT

A stable resonator for a ring-down cavity spectroscopy cell having an optic axis. The resonator includes two Brewster's angle retroreflector prisms, each having a plurality of total internal reflection surfaces, with one of the total internal reflection surfaces of at least one of the prisms having a curved surface (either a ground curved surface or a surface curved by the addition, through optically contacting or gluing, of a plano-convex lens to the surface). The prisms are disposed in alignment along the optic axis of the resonator. A spherical mirror or lens, tilted from normal incidence to produce a desired degree of astigmatism, mode matches the radiation into the resonator. One or both of the prisms can be rotated so that light rays enter and leave a surface of the prism nearly at Brewster's angle to the normal of the prism surface. This feature maintains alignment between the prisms and allows the resonator to be tuned.

22 Claims, 12 Drawing Sheets

OTHER PUBLICATIONS

D. Heriott et al., Off–Axis Paths in Spherical Mirror Interferometers, 3 *Appl. Opt.* (4), 523 (Apr., 1964).

A. O'Keefe & D. Deacon, Cavity Ring–Down Optical Spectrometer for Absorption Measurements Using Pulsed Laser Sources, 59 *Rev. Sci. Instrum.*, 2544 (Dec., 1988).

D. Romanini & K. Lehmann, Ring–Down Cavity Absorportionn Spectroscopy of the Very Weak HCN Overtone Bands With Six, Seven, and Eight Stretching Quanta, 99 *J. Chem. Phys.* (9), 6287 (Nov. 1,.

G. Rempe et al., Measurement of Ultralow Losses in an Optical Interferometer, 17 *Opt. Letters* (5), 363 (Mar. 1, 1992).

T. Yu & M. Lin, Kinetics of Phenyl Radical Reactions Studied by the "Cavity–Ring–Down" Method, 115 *J. Am. Chem. Soc.*, 4371 (1993).

G. Meijer et al., Coherent Cavity Ring Down Spectroscopy, 217 *Chemical Physics Letters* (1,2), 112 (Jan. 7, 1994).

J. Scherer et al., Cavity Ring Down Dye Laser Spectrosopy of Jet–Cooled Metal Clusters: $CU_2$ and $CU_3$, 172 *Chemical Physics Letters* (3,4), 214 (Sep. 7, 1990).

F. Stoelkel & G. Atkinson, Time Evolution of a Broadband Quasi–cw Dye Laser: Limitation of Sensitivity in Intrecavity Laser Spectroscopy, 24 *Applied Optics* (21), 3591 (Nov. 1, 1985).

K. Lehmann & D. Romanini, Molecules in the Stellar Environment, *Experimental Measurement of Weak Band Intensities in Molecules in the Stellar Environment*, (Springer, 1994).

G. Gould et al., Crossed Roof Prism Interferometer, 1 *Applied Optics* (4), 533 (Jul. 1962).

A. Pipino et al., Evanascent Wave Cavity Ring–Down Spectroscopy with a Total–Internal Reflection Minicavity, 68 (8) *Rev. Sci, Instrum.*, 2978 (Aug. 1997).

* cited by examiner

MODE MATCHING FOR CAVITY RING-DOWN SPECTROSCOPY BASED UPON BREWSTER'S ANGLE PRISM RETROREFLECTORS

This application is a continuation-in-part of U.S. patent application Ser. No. 09/412,069, filed on Oct. 4, 1999, now U.S. Pat. No. 6,097,555, which is a continuation of U.S. patent application Ser. No. 08/955,126 filed on Oct. 21, 1997, now U.S. Pat. No. 5,973,864.

FIELD OF THE INVENTION

This invention relates generally to absorption spectroscopy and, in particular, is directed to improved mode matching for ring-down cavity spectroscopy which incorporates Brewster's angle prism retroreflectors.

BACKGROUND OF THE INVENTION

Referring now to the drawing, wherein like reference numerals refer to like elements throughout, FIG. 1 illustrates the electromagnetic spectrum on a logarithmic scale. The science of spectroscopy studies spectra. In contrast with sciences concerned with other parts of the spectrum, optics particularly involves visible and near-visible light—a very narrow part of the available spectrum which extends in wavelength from about 1 mm to about 1 nm. Near visible light includes colors redder than red (infrared) and colors more violet than violet (ultraviolet). The range extends just far enough to either side of visibility that the light can still be handled by most lenses and mirrors made of the usual materials. The wavelength dependence of optical properties of materials must often be considered.

Absorption-type spectroscopy offers high sensitivity, response times on the order of microseconds, immunity from poisoning, and limited interference from molecular species other than the species under study. Various molecular species, but especially simple molecules such as water, can be detected or identified by absorption spectroscopy. Thus, absorption spectroscopy provides a general method of detecting important trace species. In the gas phase, the sensitivity and selectivity of this method is optimized because the species have their absorption strength concentrated in a set of sharp spectral lines. The narrow lines in the spectrum can be used to discriminate against most interfering species.

In many industrial processes, the concentration of trace species in flowing gas streams must be measured and analyzed with a high degree of speed and accuracy. Such measurement and analysis is required because the concentration of contaminants is often critical to the quality of the end product. Gases such as $N_2$, $O_2$, $H_2$, Ar, and He are used to manufacture integrated circuits, for example, and the presence in those gases of impurities such as water—even at parts per billion (ppb) levels—is damaging and reduces the yield of operational circuits. Therefore, the relatively high sensitivity with which water can be spectroscopically monitored is important to manufacturers of high-purity gases used in the semiconductor industry. Various impurities must be detected in other industrial applications.

Spectroscopy has obtained parts per million (ppm) level detection for water in high-purity gases. Detection sensitivities at the ppb level are attainable in some cases. Accordingly, several spectroscopic methods have been applied to such applications as monitoring water content in gases, including: absorption measurements in traditional long pathlength cells, photoacoustic spectroscopy, frequency modulation spectroscopy, and intracavity laser absorption spectroscopy. These methods have several features, discussed in U.S. Pat. No. 5,528,040 issued to Lehmann, which make them difficult to use and impractical for industrial applications. They have been largely confined, therefore, to laboratory investigations.

In contrast, cavity ring-down spectroscopy (CRDS) has become an important spectroscopic technique with applications to science, industrial process control, and atmospheric trace gas detection. CRDS has been demonstrated as a technique for the measurement of optical absorption that excels in the low-absorbance regime where conventional methods have inadequate sensitivity. CRDS utilizes the mean lifetime of photons in a high-finesse optical resonator as the absorption-sensitive observable.

Typically, the resonator is formed from a pair of nominally equivalent, narrow band, ultra-high reflectivity dielectric mirrors, configured appropriately to form a stable optical resonator. A laser pulse is injected into the resonator through a mirror to experience a mean lifetime which depends upon the photon round-trip transit time, the length of the resonator, the absorption cross section and number density of the species, and a factor accounting for intrinsic resonator losses (which arise largely from the frequency-dependent mirror reflectivities when diffraction losses are negligible). The determination of optical absorption is transformed, therefore, from the conventional power-ratio measurement to a measurement of decay time. The ultimate sensitivity of CRDS is determined by the magnitude of the intrinsic resonator losses, which can be minimized with techniques such as superpolishing that permit the fabrication of ultra-low-loss optics.

At present, CRDS is limited to spectroscopic regions where high reflectivity dielectric mirrors can be used. This has significantly limited the usefulness of the method in much of the ultraviolet and infrared regions, because mirrors with sufficiently high reflectivity are not presently available. Even in regions where suitable dielectric mirrors are available, each set of mirrors only allows for operation over a small range of wavelengths, typically a fractional range of a few percent. Further, construction of many dielectric mirrors requires use of materials that may degrade over time, especially when exposed to chemically corrosive environments. Because these present limitations restrict or prevent the use of CRDS in many potential applications, there is a clearly recognized need to improve upon the current state of the art with respect to resonator construction.

The article by A. Pipino et al., "Evanescent wave cavity ring-down spectroscopy with a total-internal reflection minicavity," Rev. Sci. Instrum. 68 (8) (August 1997), presents one approach to an improved resonator construction. The approach uses a monolithic, total internal reflection (TIR) ring resonator of regular polygonal geometry (e.g., square and octagonal) with at least one convex facet to induce stability. A light pulse is totally reflected by a first prism located outside and in the vicinity of the resonator, creating an evanescent wave which enters the resonator and excites the stable modes of the resonator through photon tunneling. The absorption spectrum of matter located at the totally reflecting surfaces of the resonator is obtained from the mean lifetime of a photon in the monolithic resonator, which is extracted from the time dependence of the signal received at a detector by out coupling with a second prism (also a totally reflecting prism located outside, but in the vicinity of, the resonator). Thus, optical radiation enters and exits the resonator by photon tunneling, which permits precise control of input and output coupling. A miniatureresonator realization of CRDS results and the TIR-ring resonator extends the CRDS concept to condensed matter spectroscopy. The broadband nature of TIR circumvents the narrow bandwidth restriction imposed by dielectric mirrors in conventional gas-phase CRDS. The work of A. Pipino et al. is only applicable to TIR spectroscopy, which is intrinsically limited to short overall absorption pathlengths, and thus powerful absorption strengths. In contrast, the present invention provides long absorption pathlengths and thus allows for detection of weak absorption strengths.

It is also possible to build a resonator out of two Brewster's angle roof prisms with crossed axes, as described in Gould et al., "Crossed Roof Prism Interferometer," Appl. Opt., Vol. 1, 533–34 (1962). The advantage of this resonator is that it remains aligned for any small angle deviation of the prisms. The disadvantage is that the Brewster's angle of one of the prisms must be set by construction, i.e., the Brewster's angle cannot be adjusted for wavelength by rotation of the prism. There are applications (e.g., at specific wavelengths) where the robust alignment of such a resonator is sufficiently desirable that the loss of the ability to tune the Brewster's angle can be tolerated. The inability to adjust Brewster's angle, however, restricts its application. Furthermore, the resonator described by Gould et al. is not optically stable, and thus cannot be used to produce a low-loss resonator, due to diffraction.

To overcome the shortcomings of the known approaches to improved resonator construction, a new high-finesse resonator (or optical resonator) for CRDS is provided. An object of the present invention is to replace the conventional dielectric mirrors with Brewster's angle prism retroreflectors, thereby providing an improved resonator. A related object is to circumvent the narrow bandwidth restriction of conventional dielectric mirrors used in CRDS. Another related object is to expand the variety of potential applications for CRDS.

It is still another object of the present invention to provide a resonator which incorporates materials that do not degrade significantly over time, even in chemically corrosive environments. An additional object is to enable "tuning," or alignment, of the resonator by rotating the prisms of the resonator. Yet another object of the present invention is to provide an innovative CRDS resonator design that achieves a low intrinsic energy loss and a well-defined relationship between photon decay time and absorption.

SUMMARY OF THE INVENTION

To achieve these and other objects, and in view of its purposes, the present invention provides a stable resonator for a ring-down cavity spectroscopy cell having an optic axis. The resonator includes two Brewster's angle retroreflector prisms, each having a plurality of total internal reflection surfaces. The prisms are disposed in alignment along the optic axis of the resonator. One or both of the prisms can be rotated independently so that light rays enter and leave a surface of the prism nearly at Brewster's angle to the normal of the prism surface. This feature maintains alignment between the prisms and allows the resonator to be tuned. One of the total internal reflection surfaces of at least one of the prisms may be a curved surface (either a ground and polished curved surface or a surface curved by the addition, through optically contacting or gluing, of a plano-convex lens to the surface). Alternatively, a lens may be centered in one arm of the resonator and tilted at Brewster's angle with respect to the optic axis of the resonator. In a preferred embodiment, each of the prisms has an apex angle of about 135° minus Brewster's angle, a second angle of about 90°, and a third angle of about 180° minus two times Brewster's angle.

The present invention also provides a resonator for a ring-down cavity spectroscopy cell having an optic axis, including a first Brewster's angle retroreflector prism having a curved internal reflection surface, a second Brewster's angle retroreflector prism in alignment with the first prism along the optic axis of the resonator, and an astigmatic optical element for coupling radiation into the resonator.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The entire disclosure of U.S. patent application Ser. No. 08/955,126, filed on Oct. 21, 1997, now U.S. Pat. No. 5,973,864, is expressly incorporated herein by reference.

Presented immediately below is an introductory summary of the general principles of modern optics relevant to the present invention. The summary is intended to provide context for a complete understanding of the invention. Those who are skilled in the art may proceed to the next section.

I. General Principles

When light travels from a first medium to a more optically dense second medium, the light is refracted toward the normal. Light approaching a rarefied medium from a dense medium is refracted away from the normal. There exists an angle, called the critical angle, $\theta_c$, such that for all angles of incidence greater than this angle, all of the light is reflected and none is transmitted. This effect is called total internal reflection (TIR) and occurs inside a material that is optically more dense than the material outside the boundary.

Figure 2:
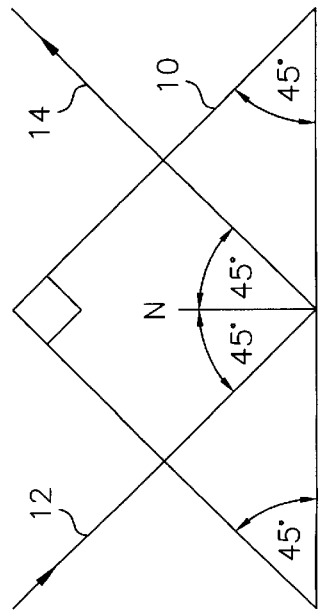
FIG. 2 illustrates total internal reflection in a prism.

A prism is one type of refractive and reflective device. As shown in FIG. 2, a prism 10 is a wedge of optical material that can either refract or totally reflect light, depending on the angle of incidence. The 45° glass prism shown in FIG. 2 is especially useful because incident light 12 entering normal to one face will totally reflect out the other face, having changed direction by 90°. Total reflection occurs because the light strikes the inner surface at 45°, which is greater than the critical angle of about 41° for glass. The line "N" represents a line normal (perpendicular) to a surface.

Figure 1:
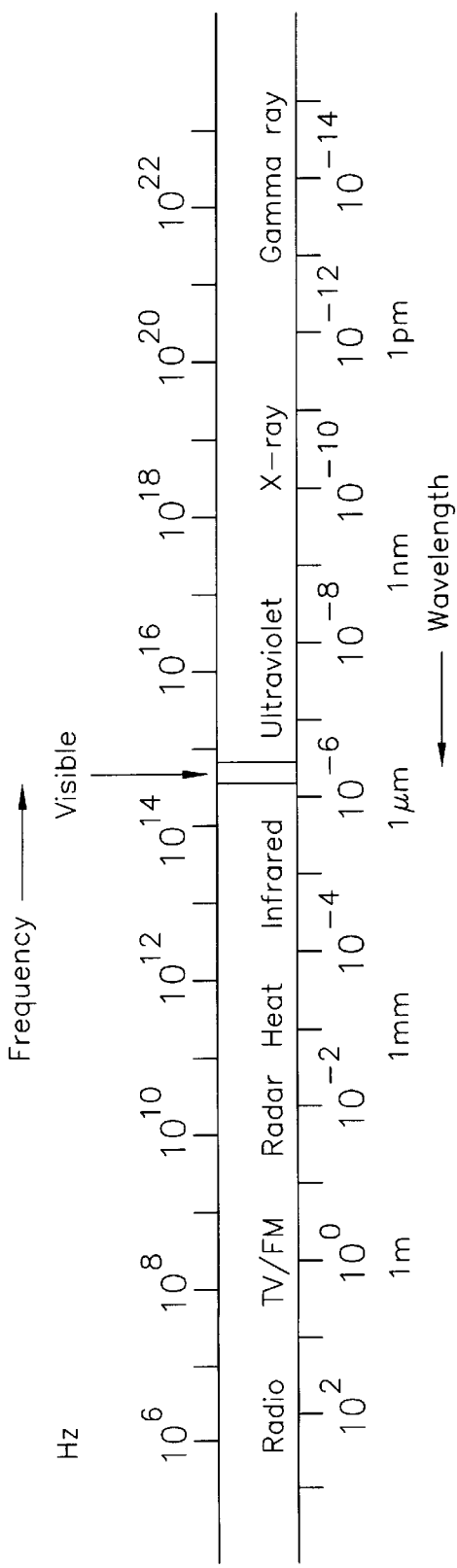
FIG. 1 illustrates the electromagnetic spectrum on a logarithmic scale.
Figure 3:
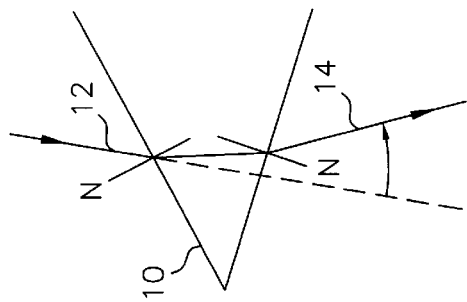
FIG. 3 illustrates deviation of light as it passes through a prism.
Figure 4:
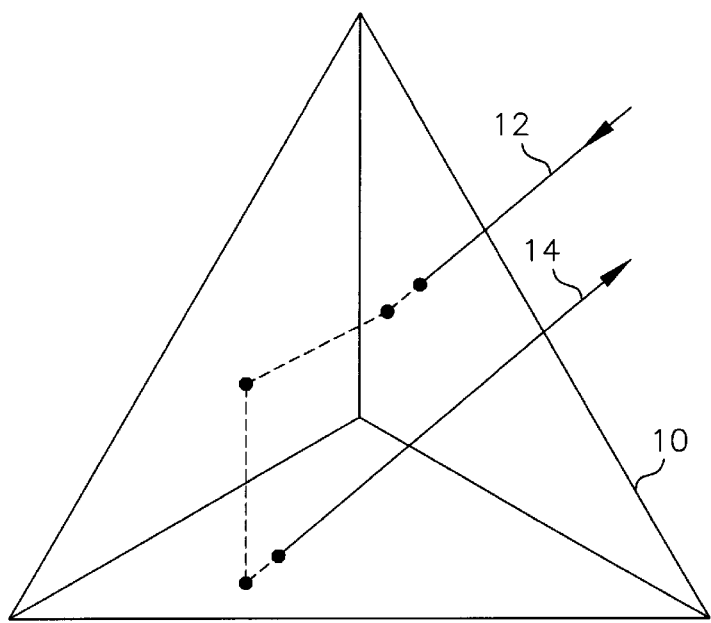
FIG. 4 illustrates how a corner reflector (retroreflector) returns light in exactly its original direction.

Light energy striking an outer surface of the prism 10 at an angle, shown in FIG. 3, is refracted in part, reflected in part by any internal surface, and refracted again as it emerges as exiting light 14. It has deviated from its original direction to emerge at a new angle. The general result is that the light is bent partly back in the direction from which it came. The deviation depends on the index of refraction of the prism, the angle of incidence, and on the angle in the vertex of the prism. For a symmetrical arrangement of incident and exiting light, 12 and 14 respectively, the angle of deviation is a minimum. More complex prisms use reflections to perform complex changes in image orientation. For example, the corner-cube prism 10 of FIG. 4 has the geometric property of sending light back exactly in the direction it came (i.e., to "retroreflect" the light).

Like all electromagnetic radiation, light is predicted by electromagnetic theory to be a transverse wave: the directions of the vibrating electric and magnetic vectors are at right angles to the direction of propagation (instead of parallel to it, as in a longitudinal wave). The transverse wave also has the characteristic that the vibrations of the electric vector are parallel to each other for all points in the wave (i.e., the wave is oriented, or polarized). In reality, incoherent (non-laser) light propagated in a given direction can consist of short, independent wavetrains whose planes of vibration are randomly oriented about the direction of propagation. Such light, although transverse, is unpolarized. Light can be partially or completely polarized by reflection.

Figure 5:
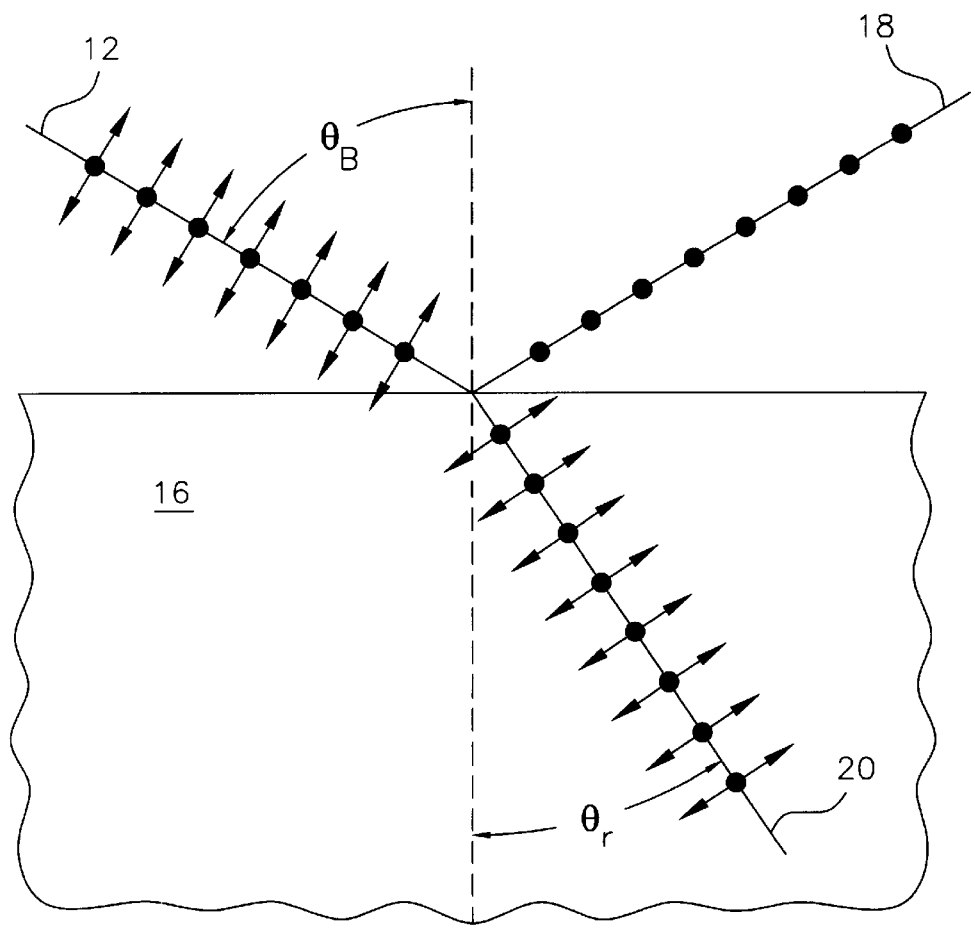
FIG. 5 illustrates an unpolarized light beam incident upon a glass surface.

FIG. 5 shows unpolarized incident light 12 traveling in air and falling on a glass surface 16. The glass has an index of refraction, n, of 1.5. The electric vector for each wavetrain in the light can be resolved into two components. One component is perpendicular to the plane of incidence, which is the plane of FIG. 5, and the other lies in the plane of incidence. The first component, represented by the dots, is the S-polarization component (from the German "senkrecht," meaning perpendicular). The second component, represented by the arrows, is the P-polarization component (for parallel). On average, for completely unpolarized light, these two components are of equal amplitude.

For glass or other dielectric materials, there is a particular angle of incidence, called the polarizing angle (also called Brewster's angle, $\theta_B$, because it was found experimentally by David Brewster), at which the reflection coefficient for the P-polarization component is zero. Thus, the light 18 reflected from the glass, although of low intensity, is plane-polarized, with its plane of vibration at right angles to the plane of incidence. The P-polarization component at the polarizing angle is entirely refracted at angle of refraction $\theta_r$; the S-polarization component is only partially refracted. Thus, the transmitted light 20, which is of high intensity, is only partially polarized.

Because light is a wave, it does not abruptly vanish on the other side of a boundary where there is total reflection. A damped non-propagating form of the wave leaks past and appears along the boundary as an "evanescent wave." This evanescent wave can be converted to a propagating wave if another surface is brought very close to the interface, within a few wavelengths. This process is called "frustrated total internal reflection."

Materials often are optically anisotropic in their response to light. In such materials, the response is different for the three independent directions possible in the material; in contrast, isotropic materials show no directional preference. For the purposes of this disclosure, materials are considered that have an identical response in two of the three directions. The third (unique) direction is referred to as the optic axis. In these materials, known as uniaxial, for light propagating in any direction except along the optic axis, the light can be resolved into two distinct waves with unique polarizations; one with the electric field oriented at right angles to the optic axis (the ordinary wave), and the other with a component of the electric field parallel to the optic axis (the extraordinary wave). These waves of different polarization refract differently in the medium, having different indices of refraction and, therefore, different speeds, which gives rise to a physical separation of the light and is referred to as double refraction or birefringence. Light that travels along the optic axis is always polarized at right angles to the axis and is purely an ordinary wave. In the more general case, with different response to light in the three spatial directions (biaxial systems), although more complex in analysis, a similar birefringence occurs. Common birefringent materials include calcite, crystalline quartz, and sapphire.

Figure 6:
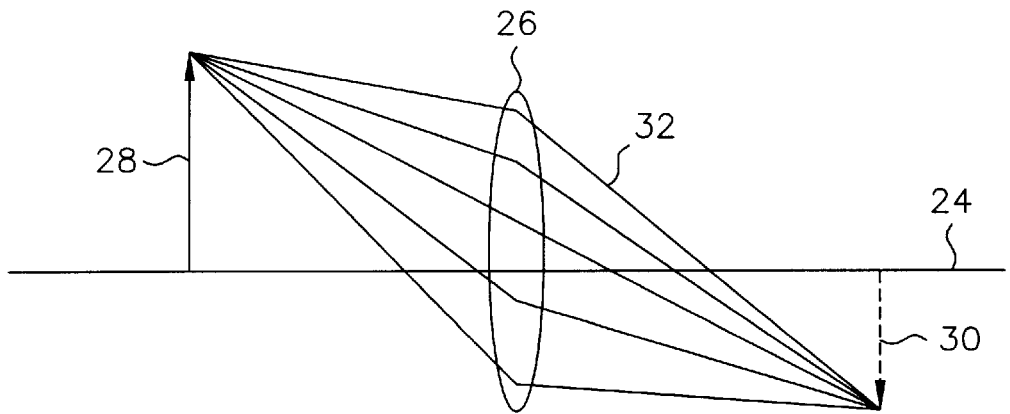
FIG. 6 is a side view of a lens, showing meridional rays and depicting how an off-axis object suffers astigmatism.
Figure 7:
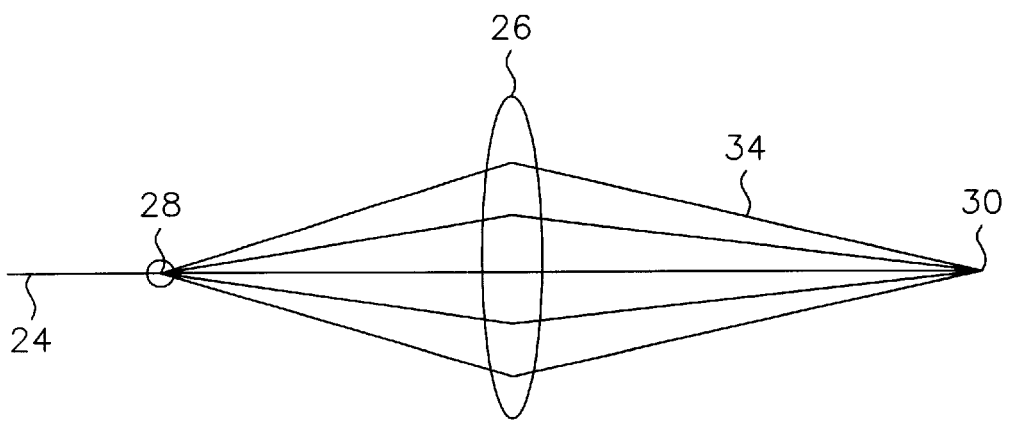
FIG. 7 is a top view of the lens shown in FIG. 6, showing sagittal rays and depicting how an off-axis object suffers astigmatism.

A lens 26 (disposed along axis 24 shown in FIGS. 6 and 7) maps each object point 28 into an image point 30. In astigmatism, the rays from off-axis object points arrive at different focal points. Consider the rays 32 from the top of the object shown in side view in FIG. 6. Rays 32 are in a meridional plane and pass through the lens 26 asymmetrically. Meanwhile, in the top view of lens 26 shown in FIG. 7, another set of rays 34 from the same point are in a sagittal plane and strike the lens 26 symmetrically. The focal points are separated for the two planes of rays, with the focal point for the sagittal rays 34 located a farther distance from lens 26 than for the meridional rays 32.

A simple way to test for astigmatism is to use a test pattern made of dots. In the two different focal planes, meridional and sagittal, there will be two different blurrings of the images of the pattern. In the meridional focal plane, the dots blur tangentially while in the sagittal focal plane the dots blur radially and form small arrows ("sagitta" is Latin for arrows) pointing toward the axis. This astigmatism occurs for spherically symmetrical lenses. These effects can be seen by this method only if the lens is free of other aberrations such as spherical and coma. Spherical aberration results in marginal rays being focused closer to the lens than axial rays; coma is an aberration where slanted rays have different focal points depending on which part of the lens they passed through.

II. The Resonator of the Present Invention

Figure 8:
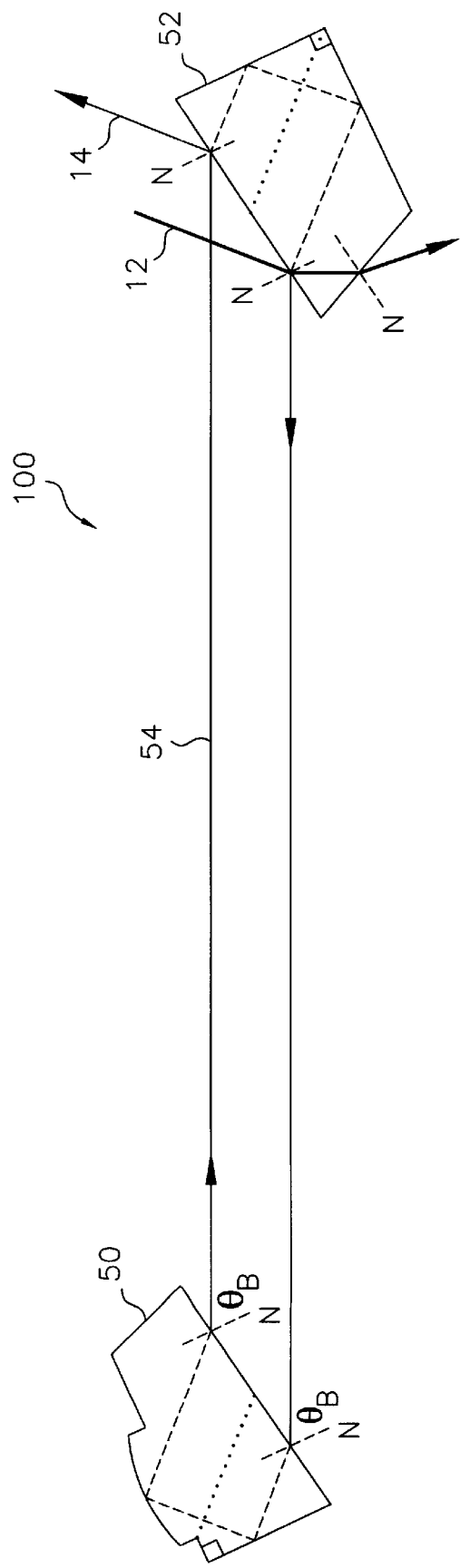
FIG. 8 illustrates the improved resonator for CRDS using two Brewster's angle retroreflector prisms in accordance with the present invention.

The present invention provides an improved resonator 100 for CRDS based upon using two Brewster's angle retroreflector prisms 50, 52 made from a high quality optical material. FIG. 8 is a schematic drawing of prisms 50, 52; optic axis 54; and the expected optical path within each prism 50, 52. The polarizing or Brewster's angle, $\theta_B$, is shown relative to prism 50. The specific angles of FIG. 8 are drawn assuming that the prisms 50, 52 are made from fused silica, although (as will be discussed below) other materials could be used instead. Incident light 12 and exiting light 14 are illustrated as input to and output from prism 52, respectively. The resonant optical beam undergoes two total internal reflections without loss in each prism 50, 52 at about 45°, an angle which is greater than the critical angle for fused quartz and most other common optical prism materials.

Resonator optical losses are caused principally by (1) scattering due to imperfections and dirt at the surfaces of prisms 50, 52; (2) residual birefringence in the optical material, due to either strain or misalignment of the optic axis of the prism substrate material; (3) misalignment from parallelism of the coupling surfaces of the prisms 50, 52; (4) deviation from Brewster's angle; and (5) internal optical transmission loss in the prism substrates due to absorption or scattering. Prisms 50, 52 can be constructed to provide low loss (i.e., less than 0.01% per round trip) over a wide range of the optical spectrum. In addition, some of the most desirable materials for use as prism substrates, including but not limited to fused silica, sapphire, and diamond, and yttrium-aluminum-garnet (YAG) are materials that are extremely hard and largely chemically inert, addressing the issue of hostile environments. Thus, resonator 100 for CRDS constructed from such prisms 50, 52 will meet and greatly expand the range of applicability of CRDS.

III. The Prism Design of the Present Invention

Figure 9A:
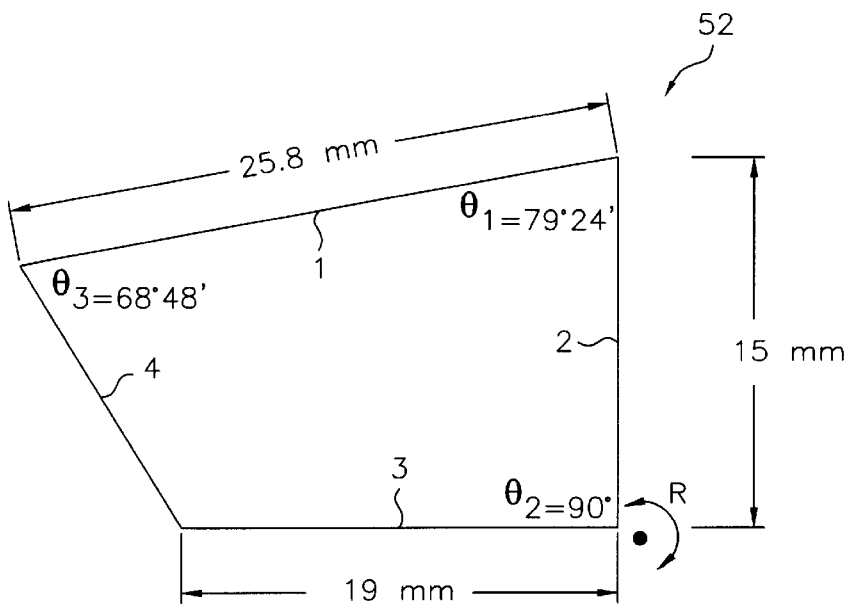
FIG. 9A is a top view of the preferred prism used in the resonator shown in FIG. 8.
Figure 9B:
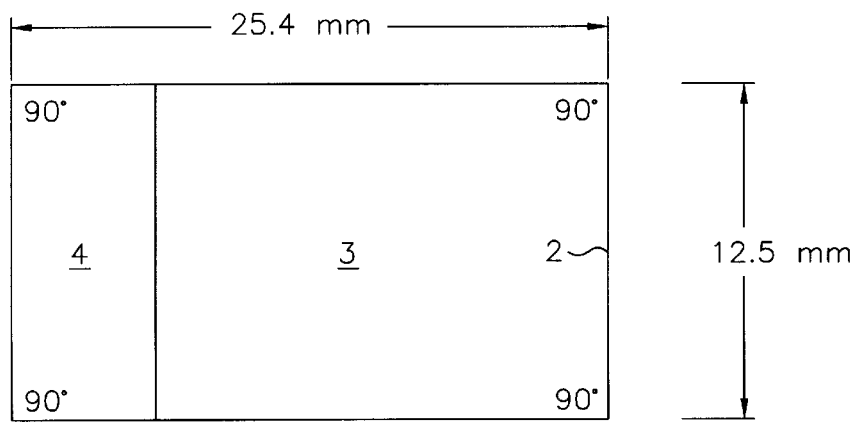
FIG. 9B is a back view of the prism of FIG. 9A.

The preferred design of prisms 50, 52 is illustrated in FIGS. 9A and 9B. Taking it as an example, prism 52 has a first surface 1, a second surface 2, a third surface 3, and a fourth surface 4. FIG. 9A is a top view of prism 52 and shows the preferred length dimensions of surface 1 (25.8 mm), surface 2 (15 mm), and surface 3 (19 mm). FIG. 9B is a back view of prism 52 and shows the preferred height dimensions of surfaces 2, 3, and 4 (12.5 mm) and the preferred width of surfaces 3 and 4 combined (25.4 mm).

For prisms constructed of material with an index of refraction "n" relative to the surrounding medium (i.e., $n=n_2 \div n_1$, where $n_2$ is the index of refraction of the prism and $n_1$ is the index of refraction of the medium surrounding the prism—typically air with $n_1=1$), Brewster's angle, $\theta_B$, is given by the arctangent of n. The value of n for the example prism 52 shown in FIGS. 9A and 9B is about 1.4607; $\theta_B$ is about 55°36'. Prism 52 has a design center of about 0.532 $\mu$m. The apex angle of prism 52 ($\theta_1$) is set equal to 135°$-\theta_B$ and, in the preferred embodiment, is about 79°24'. Angle $\theta_2$ is preferably about 90°. Angle $\theta_3$ is set equal to 180°$-2\theta_B$ and, in the preferred embodiment, is about 68°48'.

Figure 10:
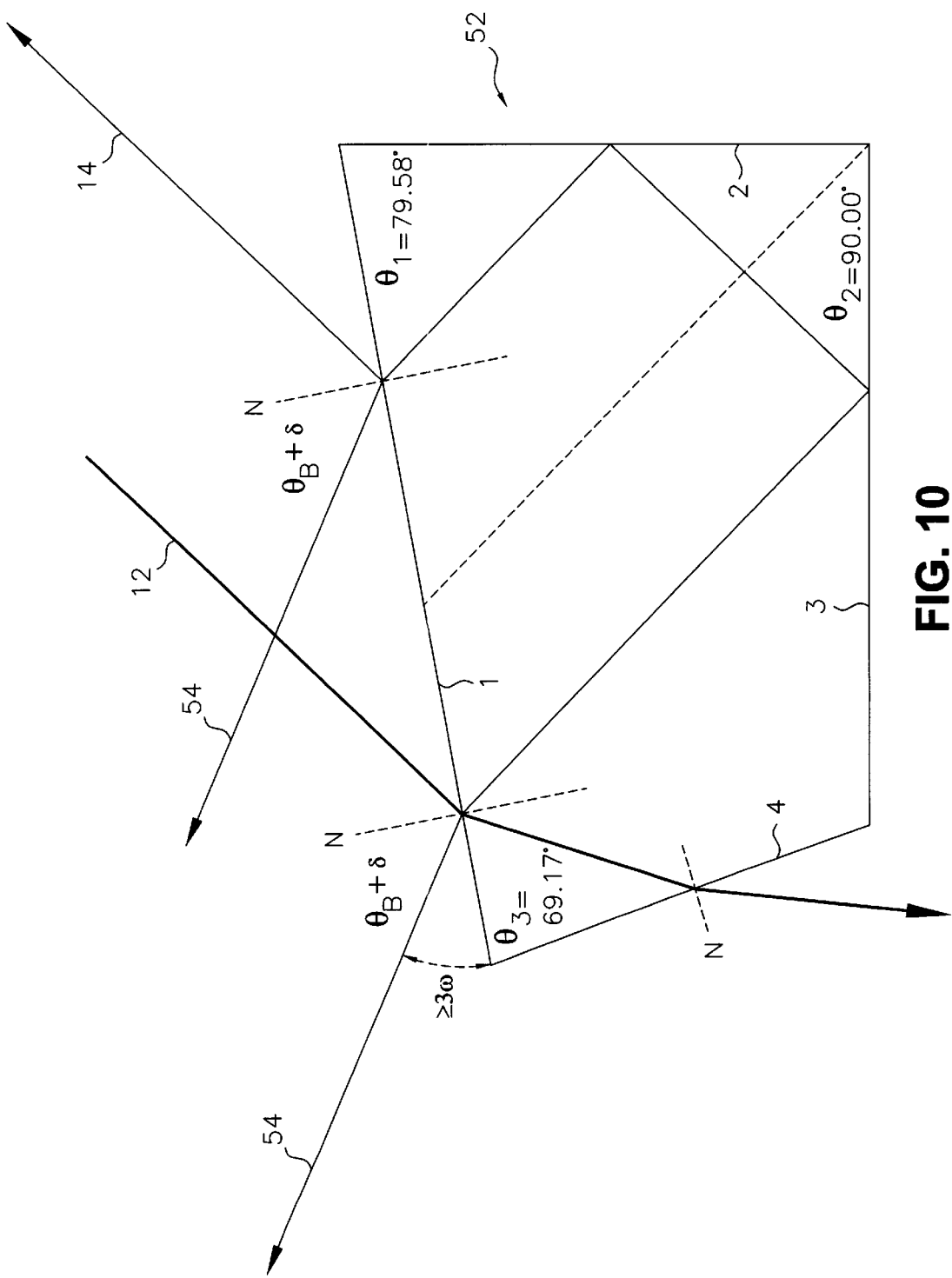
FIG. 10 shows how light incident rays enter and leave the prism, constructed in accordance with the present invention, nearly at Brewster's angle to the normal of the prism surface (with angles calculated for a prism made of fused silica)

FIG. 10 shows that rays of incident light 12 enter prism 52, and leave as rays of exiting light 14, nearly at Brewster's angle (within a small deviation, δ) to the normal "N" of surface 1. This results in small but controlled reflection loss for optical radiation with P-polarization with respect to the Brewster's angle surface. The value of n for the example prism 52 shown in FIG. 10 is approximately 1.45047; $\theta_B$ is about 55°25'. Prism 52 has a design center of 1 $\mu$m. Any optical radiation in the S-polarization is rapidly damped due to large reflection loss. The symbol "ω" characterizes the size of the spot generated by the light beam; negligible "clipping" of the beam occurs. The spot size for the lowest order mode can be calculated from standard optical resonator theory. For the prism 52 illustrated in FIG. 10, the apex angle ($\theta_1$) is preferably about 79°35' (or 79.58°). Angle $\theta_2$ is preferably about 90°. Angle $\theta_3$ is set equal to about 69°10' (or 69.17°).

IV. Material of Construction

The choice of optimal material for use in the construction of the prisms 50, 52 will depend upon the particular application. In order to allow for polishing of the surfaces to the required tolerances, a "hard" and chemically stable substrate material is needed. Also desirable is a material that has both low absorption and scattering loss over the spectral region of interest. Although five substrate materials are known to be suitable, namely fused silica, sapphire, calcium fluoride, diamond, and yttrium-aluminum-garnet (YAG) the present invention is not limited to these specific materials.

Fused silica is an excellent material which is widely used in the optics industry for construction of precision optical components. It has low absorption loss over a wide range of wavelengths. Because it is a glass, however, fused silica has frozen disorder on the molecular level that leads to significant Raleigh scattering loss, especially in the ultraviolet region.

Single crystal sapphire substrates are available and can also be manufactured to precision specifications. Sapphire has a wider spectral range of low absorption loss than fused silica; the highest quality samples have almost negligible scattering loss throughout the visible and into the near-ultraviolet region. Sapphire is a birefringent material and, to prevent excess loss due to polarization rotation within the resonator optics, the unique optic axis must be oriented along the axis perpendicular to the plane in FIG. 9A. This can be done to the required tolerance. The natural birefringence characteristic of sapphire is advantageous because the material is less susceptible to losses from strain birefringence which typically are the result of imperfect mechanical mounting of the prisms.

Sapphire is likely the material of choice for most applications. Diamond would in many ways be the ideal substrate material, except for the high cost of the material and processing.

V. Tuning

The use of "roof" retroreflectors renders a prism optical resonator alignment insensitive to small rotation of the prisms around the roof line and makes for a more robust alignment. Such a resonator can be constructed using Brewster's angle roof prisms with crossed axes. The advantage of this resonator is that it remains aligned for any small angle deviation of the prisms. The disadvantage is that the Brewster's angle of one of the prisms must be set by construction, i.e., it cannot be "tuned" by rotation of the prism around the roof axis. The resonator 100 of the present invention avoids that disadvantage.

Resonators can be characterized by a quality factor, Q, defined as the energy stored divided by the energy lost per cycle. Resonators with higher "Q" values are better at conserving energy and thus lead to higher sensitivity in cavity ring-down spectroscopy. According to the present invention, the resonator "Q" and coupling are controlled by tilting the prisms 50, 52 to adjust the level of reflection loss.

The reflection loss per surface is determined by the Fresnel relations, and is approximately $10^{-4}\ \delta\theta^2$, where $\delta\theta$ is the deviation from Brewster's angle in degrees.

Light rays undergo two internal bounces at prism surfaces 2 and 3, and then leave the prism 50, 52 by transmission at surface 1. If angle $\theta_2$ is constructed to be 90°, the input rays or incident light 12 and output rays or exiting light 14 of the prism 50, 52 will be parallel but displaced if contained in the plane of FIG. 9A. The angles of incidence of both the rays of incident light 12 and the rays of exiting light 14 are equal, and can be tuned by rotation of the prism about the axis "R" normal to the plane in FIG. 9A. One approach to providing a mechanism for rotation of the prism is disclosed, in a generic sense, in FIG. 3 and at column 7, lines 14–30, of U.S. Pat. No. 5,483,343 issued to Rockwell. It is understood that the prisms 50, 52 have been aligned such that the roof lines forming the 90° angles are normal to the plane of FIG. 9A. As the prism 50, 52 is rotated, the angle of incidence for the internal reflections will increase by the same angle on one surface, and decrease by an equal amount on the other. In order to make these two total internal reflection angles approximately equal, the apex angle of the prism ($\theta_1$) should be constructed to be equal to $135°-\theta_B$.

For prisms made of fused quartz, Brewster's angle varies from 55.5–57.1° as the wavelength is varied from near-infrared to the onset of the vacuum ultraviolet (200 nm) while the critical angle varies from 43.4° to 40.31°. As a result, one pair of prisms 50, 52 can be designed to provide total internal reflection while allowing the tilt to reach Brewster's angle over that range of wavelength. By selecting angle $\theta_3$ to be equal to $180°-2\theta_B$, an optical beam coupled into the resonator by reflection from surface 1 will propagate through the crystal and also leave through surface 4 with an angle of incidence near Brewster's angle. This will reduce the amount of light energy that is reflected inside the prism that could be a source of unwanted stray light energy.

VI. Stability Control

Figure 11:
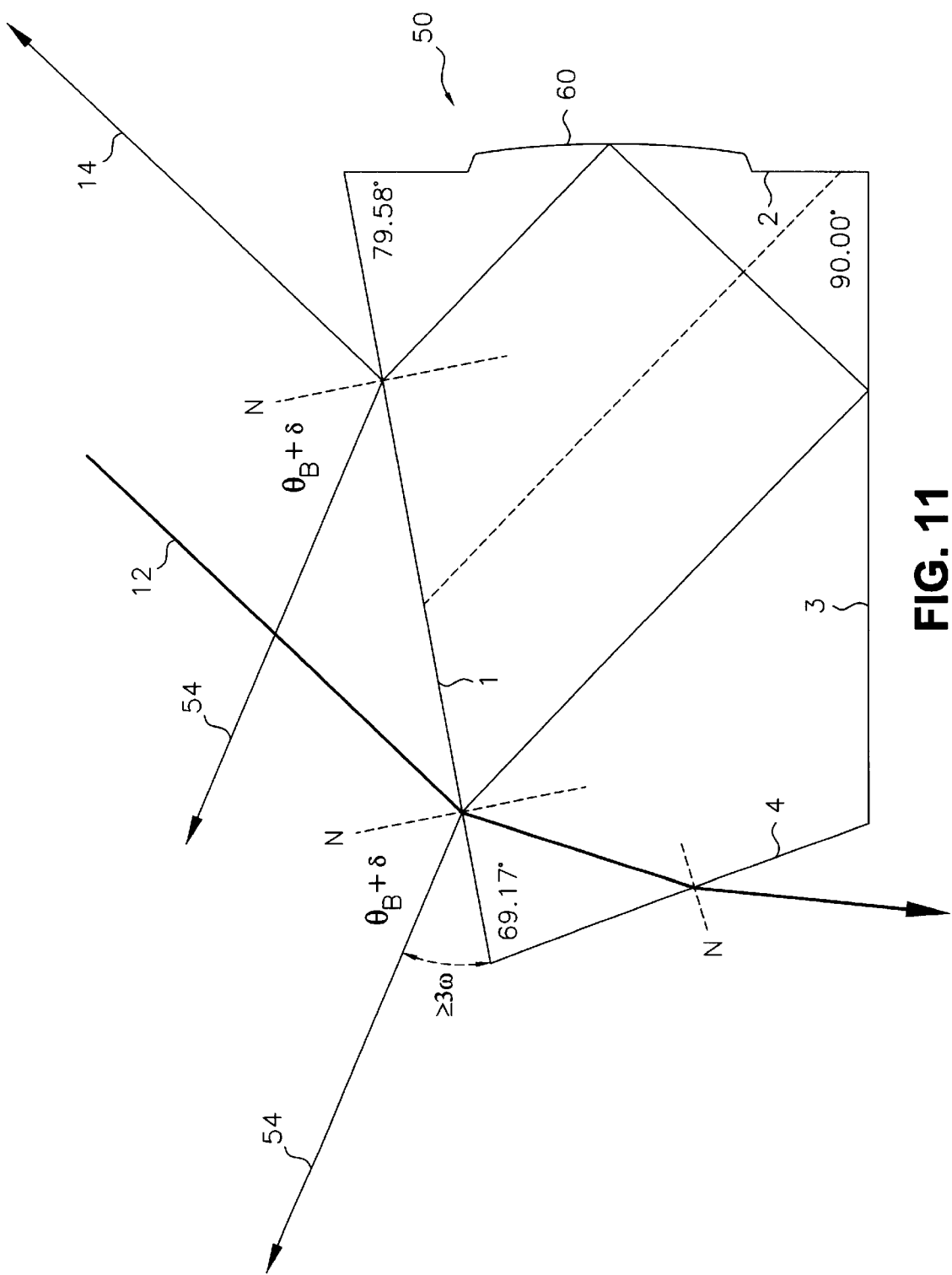
FIG. 11 depicts one of the total internal reflection surfaces on one prism ground with a curvature according to the present invention.

Optical resonator 100 is formed from a pair of prisms 50, 52 which act as retroreflectors. To form a stable optical resonator 100, and thus control the diffraction of the optical beam as it bounces back and forth, at least one of the total internal reflection surfaces on one prism is configured with a curvature. Such a curved surface 60 is shown in surface 2 of prism 50 in FIG. 11.

To correct for the astigmatism produced both by the Brewster's angle surface and reflection from the curved surface near 45°, the tangential curvature of curved surface 60 must be $2n^2\sqrt{2}$ f and the sagittal curvature (i.e., the curvature in the plane normal to that of FIG. 11) must be $\sqrt{2}$ f, where f is the desired effective focal length of the curved surface 60. The focal length, f, is selected to be approximately equal to the separation distance between the two prisms, 50, 52, which is on the order of 1 meter in the preferred embodiment, to form a nearly half or folded confocal resonator 100.

Such an astigmatically compensated resonator 100 will have stable resonant modes that are cylindrical symmetric, simplifying the design of the mode-matching optics that are used to couple the radiation into the optical resonator 100. It will be appreciated that the construction of such a prism 50 may be difficult because it requires polishing and centering an astigmatic lens of precise curvature onto one of the prism surfaces. A simple spherical surface ground into one prism surface, such as surface 2, can be used with a curvature selected to give stability for rays with sagittal deviation from the optic axis 54 of the resonator. The presence of a focusing element inside the resonator 100 also compensates for small errors in the manufactured angles and the positioning of the prisms, 50, 52, maintaining stability and low loss despite small deviations of the optic axis 54. In the latter case, the resonator eigenmodes will not be cylindrically symmetric.

Figure 12:
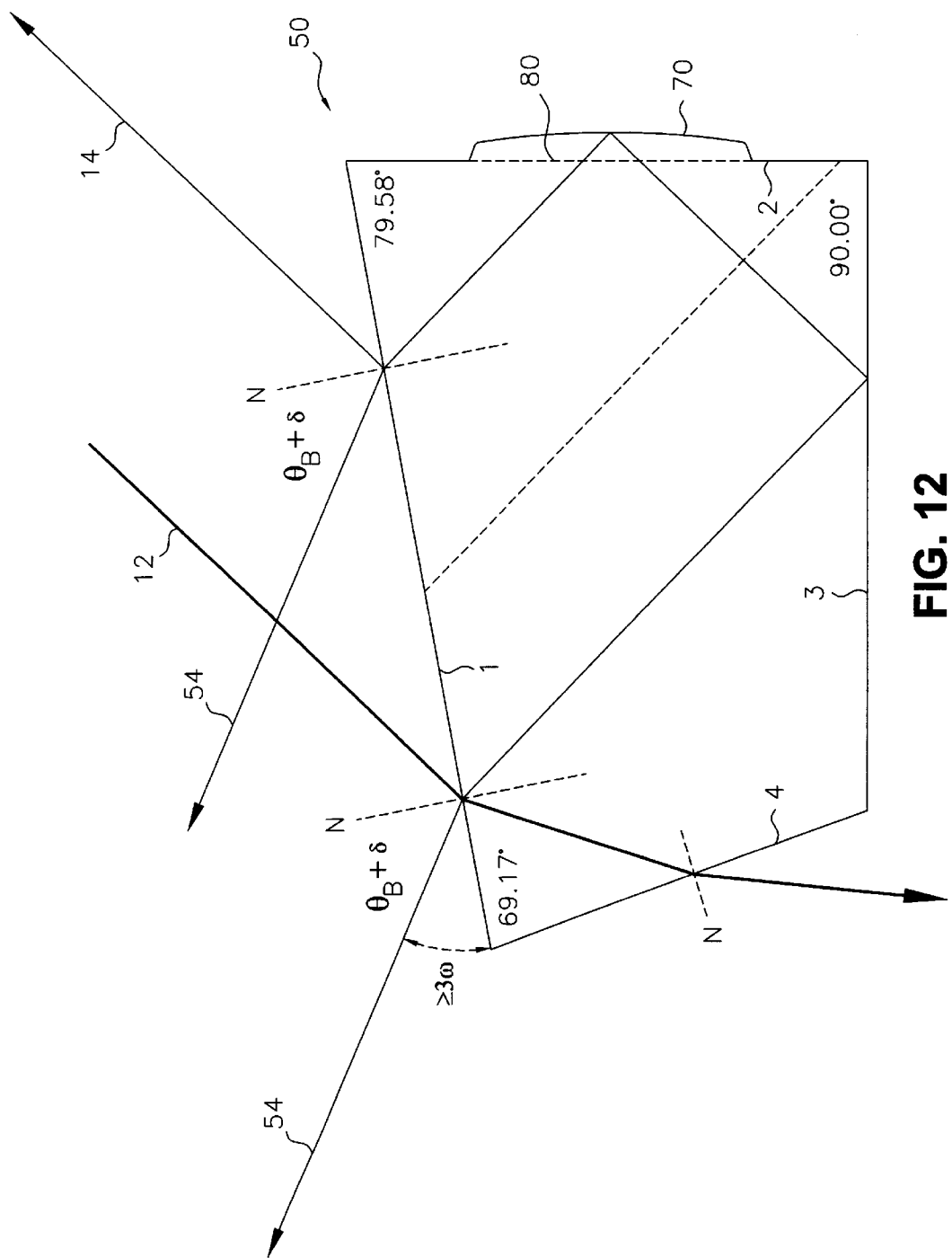
FIG. 12 shows a plano-convex lens optically contacted or glued to a prism surface according to the present invention.

Alternatively, as shown in FIG. 12, fabrication of prism 50 may be simplified by following a two step procedure. First, the prism 50 is fabricated with purely planar surfaces 1, 2, 3, and 4. Then a plano-convex lens 70 is made of the same material as prism 50 and of the appropriate astigmatism. The plano surface of the lens 70 is optically contacted to a prism surface (e.g., surface 2). When optically contacted, the interface between the components disappears, eliminating losses and providing optical performance equivalent to a monolithic (or integral, or one-piece) structure. When working with near-infrared and visible wavelengths, the lens 70 can be glued to the surface 2 of prism 50 with index-matching optical cement 80 which is a much simpler procedure than optical contacting.

Figure 13:
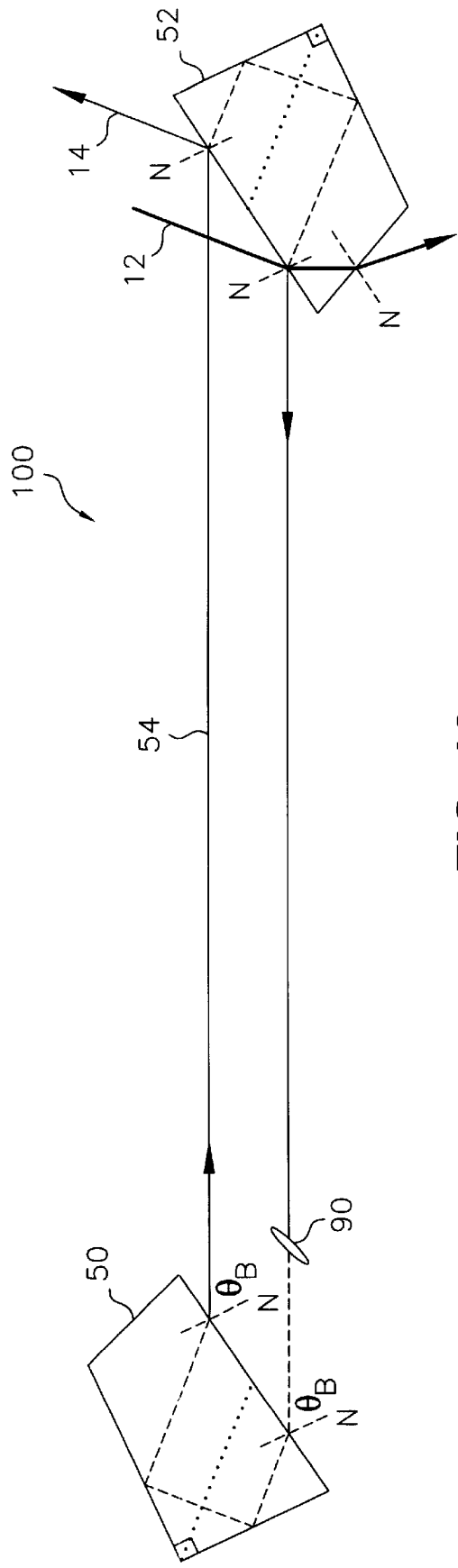
FIG. 13 illustrates a lens centered in one arm of the ring resonator, and tilted at Brewster's angle with respect to the optic axis, according to another embodiment of the present invention.

An additional variation is, as shown in FIG. 13, to separate the lens completely from the body of either prism 50, 52. In this case, the astigmatic lens 90 is centered in one arm of the ring resonator 100 and tilted at Brewster's angle with respect to the optic axis 54, producing no reflection losses. The sagittal and tangential curvature are arranged to compensate for astigmatism while providing appropriate curvature for optical stability. As described below, the coupling is provided from one of the plano surfaces 1, 2, or 3 of the prisms 50, 52.

In the first exemplary embodiment a pair of right angle prisms with Brewster's angle interfaces constitute the reflective optics of the resonator 100. It is understood that with few exceptions, modes of the resonator are spatially elliptical. This is a result of astigmatism introduced by the transmission through the Brewster's angle surfaces and also the reflection at non-normal incidence from the curved totally reflecting surface that is used to provide optical stability for the resonator. In the preferred embodiment of FIG. 8, an astigmatic curvature 60 (shown in FIG. 11) is polished into the corrective surface of prism 50 to compensate for the astigmatism and render the modes circular. This is done to improve the coupling efficiency and reduce the instabilities in the ring down rate of the resonator when used with lasers that have circular beam profiles. It is expensive, however, to polish a proscribed astigmatism into a prism surface with the accuracy needed for matching a circular profile to the resonator. One approach, although relatively expensive, is to use a telescope with astigmatic lenses to solve the problem.

Figure 14:
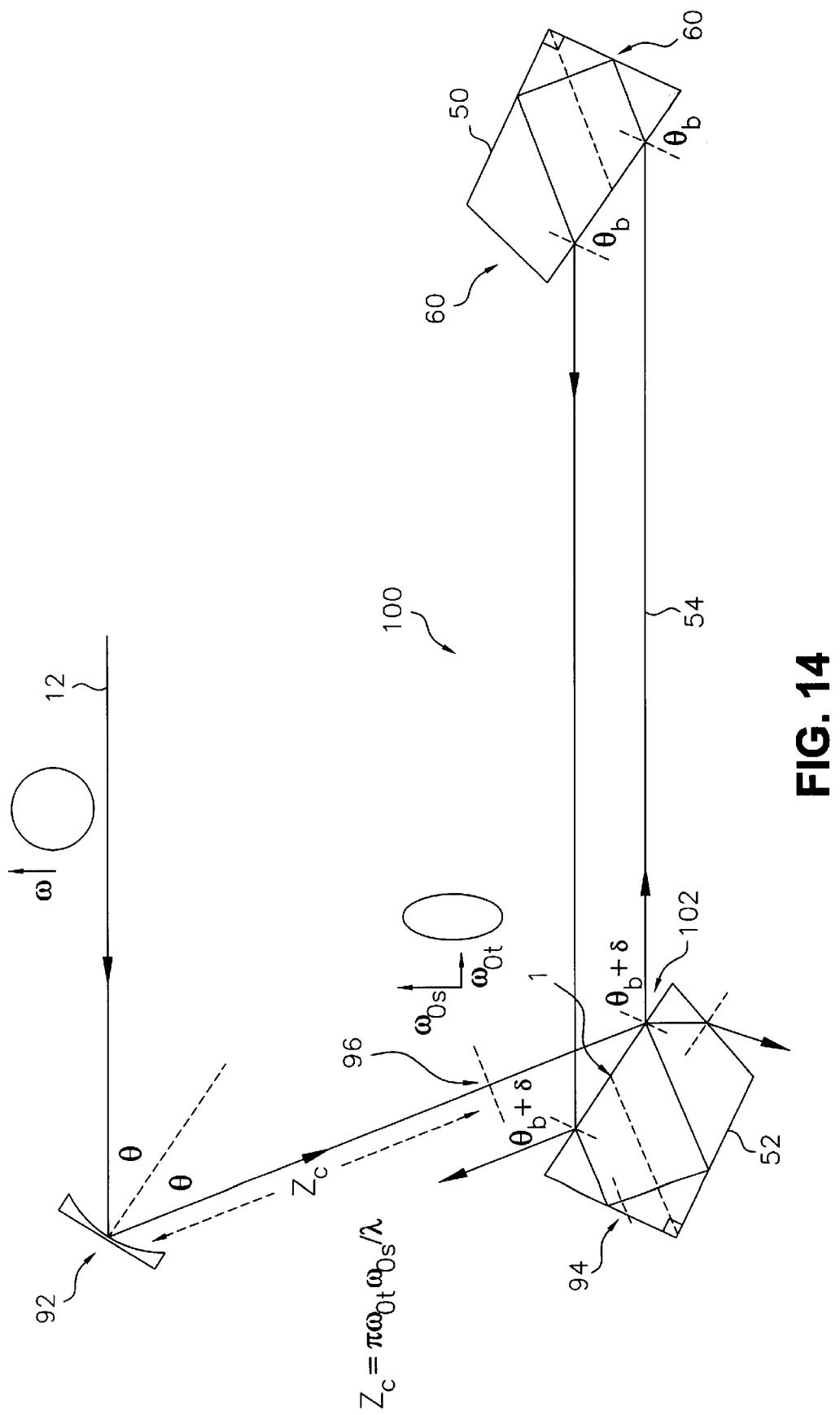
FIG. 14 illustrates an off-axis spherical mirror coupling radiation into the ring resonator according to yet another embodiment of the present invention.

A more cost effective and flexible approach to solve the coupling problem is shown in the exemplary embodiment of FIG. 14. Consider the embodiment with the resonator 100 constructed having a spherical curvature polished 60 into one of the internal reflecting surfaces of prism 50. Because of the astigmatism produced when rays strike the spherical surface at or near a 45° angle of incidence, the minimum spot size, $\omega_{0t}$, for tangential rays (those in the plane of the figure) will be smaller than that for sagittal rays (those orthogonal to the plane), $\omega_{0s}$. The exact values for the tangential and sagittal spot sizes may be calculated for the resonator using the ABCD matrix as described, for example, in *Lasers,* by A. Siegmann, page 820, eqs. 14, 15, University Science Books, Sausalito, Calif., 1986.

Because the angular spread of a resonator mode either leaving or entering the resonator is greater for the tangential rays, which have a smaller spot size at the resonator waist 94 than the sagittal rays, the beam will grow more rapidly in the tangential direction. The resonator waist 94 is a plane located near the center of the prism 52 that has all planer surfaces and constitutes the optical center of the resonator 100 as shown in FIG. 14. As a result of this difference in growth, the spot size for the two sets of rays are equal and the beam will be circular at a specific point outside the resonator 100. The location of that point is calculable in terms of the resonator parameters, specifically, the Rayleigh ranges of the sagittal and tangential rays of the resonator mode. In FIG. 14, for the incoming beam 12, it is shown that the resonator waist 94 is located a distance behind the surface 1 which reflects the input beam 12 into the resonator 100. As a result, there is an effective input waist 96 outside the resonator at an equal optical distance from the surface 1 as the true resonator waist.

The distance from the effective input waist 96 to the entry point 102 is based on the optical distance from the resonator waist 94 to the entry point 102. This optical distance is the physical distance from resonator waist 94 to entry point 102 multiplied by the index of refraction of prism 52. In the preferred exemplary embodiment, the optical distance from the resonator waist 94 to the entry point 102 is approximately equal to the physical distance from the effective input waist 96 to the entry point 102. This is because resonator 100 is in air where the index of refraction is unity. If resonator 100 is in a medium other than air, the optical distance between the effective input waist 96 to the entry point 102 would depend on the index of refraction of the medium. In this case, the optical distance between the effective input waist 96 to the entry point 102 would be approximately equal to the optical distance between the resonator waist 94 and the entry point 102.

It is also clear from FIG. 14 that the input and output could be interchanged with an appropriate change in position of the astigmatic optical element 92. In addition, one could use the prism 50 with the curved surface 60 as the coupling prism. This would necessitate bringing the astigmatic optical element 92 closer to the resonator 100 since the prism 50 with the curved face 60 is further from the resonator waist. This may be desirable for a more compact design.

To calculate the position 96 at which the spots are equal, we use the following equations that describe the propagation of Gaussian beams within the paraxial approximation: The Rayleigh range $z_0$ is given by equation (1):

$$z_0 = \pi \omega_0^2 / \lambda \qquad (1)$$

where $\omega_0$ is the minimum spot size at the resonator waist 94 (the spot size being the beam radius at which the optical field falls to 1/e of its peak value for the lowest order mode), and $\lambda$ is the wavelength of the light. The square of the spot size at any other position of the propagating mode is given by equation (2):

$$\omega^2 = \omega_0^2 [1 + (z/z_0)^2], \qquad (2)$$

where z is the distance measured from the waist. And finally, the radius of curvature r of the optical field at a distance z from the waist is given by equation (3):

$$r = z_0(z/z_0 + z_0/z), \qquad (3)$$

If we now use equation (2) for both the sagittal and tangential rays and require an equality, we obtain equation (4):

$$\omega_{0s}^2[1+(z/z_{0s})^2] = \omega_{0t}^2[1+(z/z_{0t})^2], \qquad (4)$$

Substituting equation (1) into (4) for the value of $z_{0t}$ and $z_{0s}$, we obtain equation (5) for the distance, $z_c$, as measured from the waist for equal spot size (circular beam):

$$z_c = \pi \omega_{0s} \omega_{0t} / \lambda, \qquad (5)$$

$z_c$ is equal to the Rayleigh range for a beam with a spot size that is the geometric mean of the tangential and sagittal spot size.

The second step is to place a lens or mirror 92 with optical power at the position of equal spot size and then adjust the angle of incidence $\theta$ to compensate for the modal astigmatism. To understand the compensating effect of the lens or mirror, we can envision a circular beam entering the resonator and being made astigmatic to match the resonator mode, or conversely consider the astigmatic mode leaving the resonator and being converted into a circular Gaussian mode. For convenience, we consider the beam to be leaving the resonator, but it should be understood that the result is equally applicable to its inverse. For our purpose we require that the optical element act in such a way as to produce an equal radius of curvature for the tangential and sagittal rays of the emerging beam. This will ensure that the mode remains circular from that point on, provided there are no additional astigmatic elements in the path. Further mode matching to different spot size and curvature can easily be accomplished on the circular beam using telescopes or other means familiar to those skilled in the art. The simple lens formula for non-normal incidence on a lens or mirror for the tangential and sagittal rays respectively is given by equations (6) an (7):

$$1/r_{et} = 1/r_{it} - 1/f \cos \theta, \qquad (6)$$

and $$1/r_{es} = 1/r_{is} - \cos \theta / f, \qquad (7)$$

where $r_{et}$ and $r_{es}$ are the radii of curvature of the exiting tangential and sagittal rays, $r_{it}$ and $r_{is}$ are the incident radii of curvature, f is the focal length of the lens or mirror and $\theta$ is the angle of incidence. A positive value for f indicates a focussing lens or mirror. An expanding beam in the direction of propagation has a positive radius of curvature while a converging beam has a negative radius of curvature. From equation (3), substituting the values for the incident radii of curvature into equation (6) and (7) and equating them, we obtain equation (8) for the value of f and $\theta$ that produces equal exiting radii of curvature and, hence, a circular beam. We are restricted for a physical solution, however, to the range of angles $0 \leq \theta \leq 90°$ which means that $0 \leq \cos \theta \leq 1$.

$$\cos^{-2} \theta + f \cos \theta (\omega_{0s}^2 - \omega_{0t}^2) / [z_c(\omega_{0s}^2 + \omega_{0t}^2)] - 1 = 0 \qquad (8)$$

Replacing the ratio $\omega_{0s}/\omega_{0t}$ with $\alpha$, a value always greater than unity, the quadratic equation can be rewritten as equation (9):

$$\cos^2 \theta + f \cos \theta (\alpha^2 - 1) / z_c (\alpha^2 + 1) - 1 = 0 \qquad (9)$$

The general solution of the quadratic equation (9) is given by equation (10):

$$\cos \theta = \frac{-f(\alpha^2 - 1)}{2z_c(\alpha^2 + 1)} \pm \left( \frac{f^2(\alpha^2 - 1)^2}{4z_c^2(\alpha^2 + 1)^2} + 1 \right)^{1/2} \qquad (10)$$

The terms within the radical are always positive because they are the square of real numbers. For positive values of f, it is easy to see that for any magnitude of f, there is one unique solution for $\cos \theta$ that is bounded by 0 and +1, and hence, an angle of incidence exists which will satisfy the equation and produce a circular beam. For negative values of f there is no angle θ that will work. If one is willing, however, to reflect the beam out of the plane, that is e.g., in FIG. 14, turning the mirror 92 so that the beam is reflected out of paper, then the sagittal and tangential focal lengths of the mirror have interchanged, and a negative focal length mirror may be used to produce a circular beam.

In order to avoid grazing incidence reflection or transmission and possibly go beyond the paraxial approximation, extreme focal lengths should not be used, either short or long, for the lens or mirror 92. With this in mind, in the preferred embodiment, the angle of incidence θ is less than about 60°, and an appropriate focal length for the mirror or lens 92 is chosen to satisfy that condition.

Figure 15:
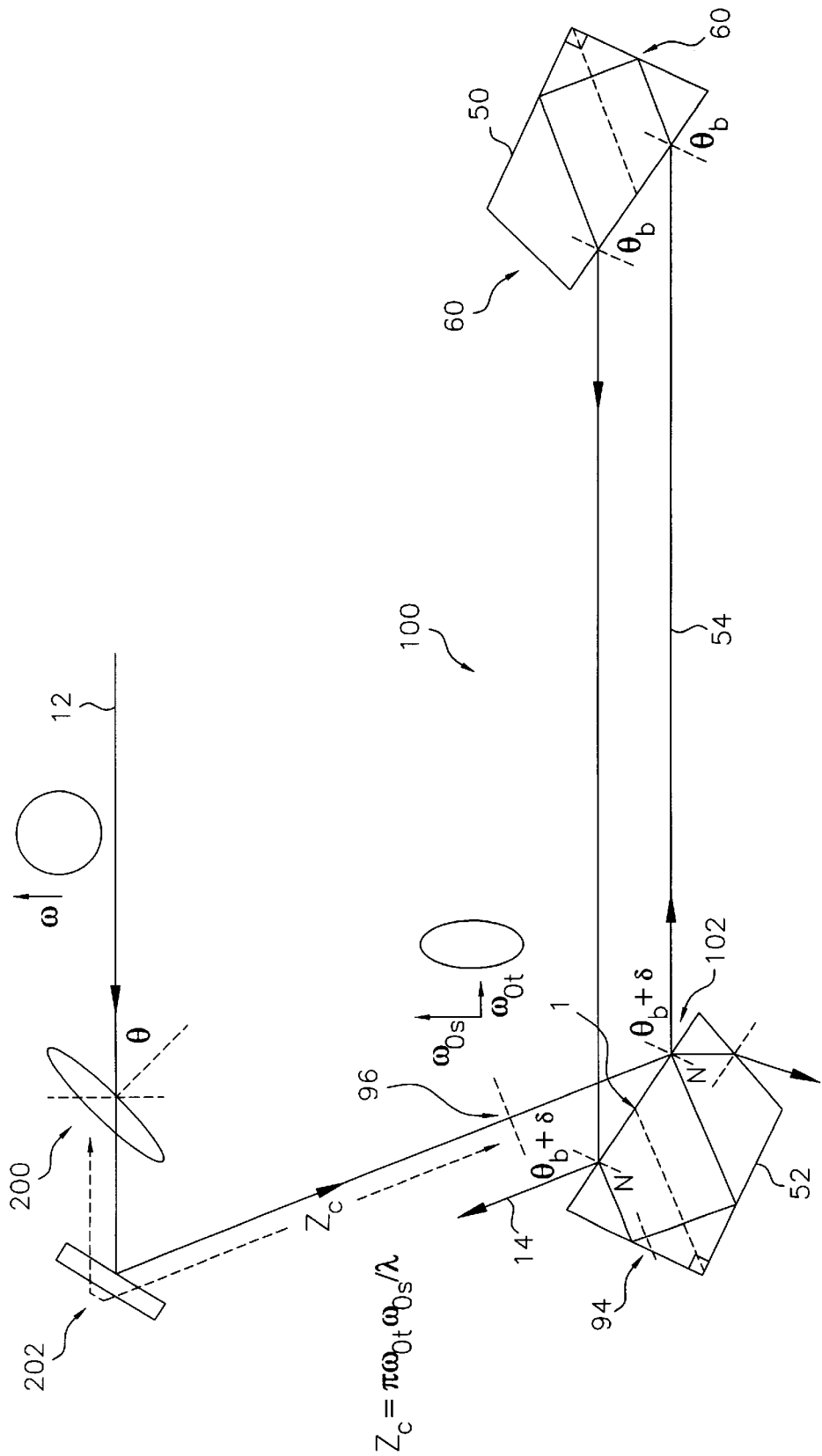
FIG. 15 illustrates an off-axis spherical lens and a reflective surface coupling radiation into the ring resonator according to a further embodiment of the present invention.
Figure 16:
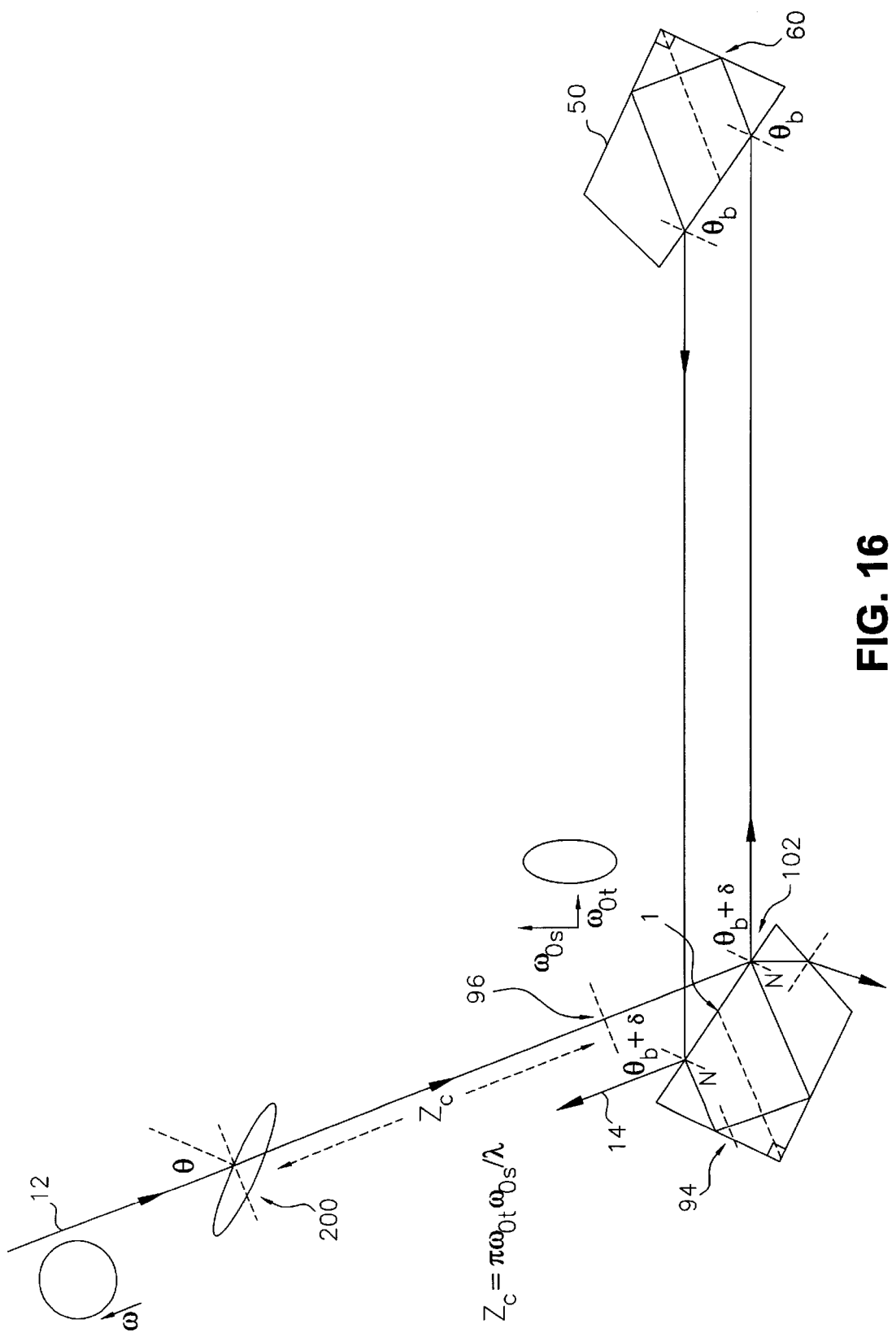
FIG. 16 illustrates a spherical lens coupling radiation directly into the ring resonator according to yet another embodiment of the present invention.

Referring now to FIG. 15 a further exemplary embodiment of the present invention is illustrated. In FIG. 15, a spherical lens 200 tilted at an angle θ to input beam 12 is inserted into input beam 12. To keep the input beam 12 approximately parallel to optic axis 54 a reflector 202, such as a mirror, redirects the input beam 12 after it passes through spherical lens 200 so that the input beam 12 is directed toward prism 52 of resonator 100. In this embodiment, the distance $z_c$ is measured from spherical lens 200 to effective waist 96. Furthermore, the angle of reflector 202 is irrelevant and may be any angle that allows input beam 12 to strike a reflective surface of reflector 202. It should be noted that reflector 202 is not required, and may be eliminated. In such a case, spherical lens 200 is placed directly in the path of input beam 12 as shown in FIG. 16.

Radiation can be coupled into the resonator 100 in one of two ways. Frustrated total internal reflection can be used at one of the flat internal reflecting surfaces 2 or 3—or the prism 50, 52 can be tilted slightly away from Brewster's angle—provide coupling from surface 1. The second method is technically easier but produces twice the loss for a given coupling parameter. The resonator 100 forms a ring and has no standing waves if light is coupled into it in one direction. Consequently, when one prism surface is rotated about its roof axis away from Brewster's angle to provide a means for coupling, the output from the same surface is spatially separated from the input, allowing for ease in separating the weak output beam from the intense input.

The use of a ring resonator 100 has certain additional advantages because it greatly reduces the level of optical radiation feedback to the source. Such feedback can potentially destabilize the source laser requiring the use of high precision optical isolators which themselves are of limited spectral bandwidth and add to overall system complexity and cost. The resonator 100 according to the present invention allows, for the first time, a broad bandwidth CRDS resonator to be constructed. Resonator 100 will clearly expand both scientific and commercial applications for CRDS spectroscopy. The broad spectral bandwidth of the improved CRDS resonator will allow for development of multispecies sensors.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A resonator for a ring-down cavity spectroscopy cell having an optic axis, the resonator comprising:
   a first Brewster's angle retroreflector prism having a plurality of total internal reflection surfaces with one of the total internal reflection surfaces being a curved surface;
   a second Brewster's angle retroreflector prism having a plurality of total internal reflection surfaces and being disposed in alignment with the first prism along the optic axis of the resonator; and
   an optical element for coupling radiation into one of the first and second prisms.

2. The resonator as recited in claim 1, wherein the optical element has an astigmatic property.

3. The resonator as recited in claim 2, wherein the optical element is at least one of a lens and a mirror, the radiation being incident on a surface of the optical element.

4. The resonator as recited in claim 3, wherein the optical element has a positive focal length.

5. The resonator as recited in claim 2, wherein the optical element is one of a lens and a mirror having a negative focal length, the radiation being incident on a surface of the optical element.

6. The resonator as recited in claim 5, wherein the optical element is tilted out of a plane determined by the optic axis of the resonator.

7. The resonator as recited in claim 1, wherein the prisms are one of fused silica, sapphire, diamond, calcium fluoride, and yttrium-aluminum-garnet (YAG).

8. The resonator as recited in claim 1, wherein a reflected radiation from the optical element has a sagittal ray and a tangential ray, the reflected radiation having a circular cross-section at a position $z_c$ from the optical element.

9. The resonator as recited in claim 8, wherein the position $z_c$ is $\pi\omega_{0s}\omega_{0t}/\lambda$, where $\lambda$ is the wavelength of the radiation, $\omega_{0s}$ is a minimum spot size of the sagittal ray, and $\omega_{0t}$ is a minimum spot size of the tangential ray.

10. The resonator as recited in claim 1, wherein each of the prisms has an apex angle of about 135° minus Brewster's angle, a second angle of about 90°, and a third angle of about 180° minus two times Brewster's angle.

11. The resonator as recited in claim 1, further comprising an effective waist point that lies along an axis of the radiation between the second Brewster's angle retroreflector prism and the optical element and, the second Brewster's angle retroreflector prism includes an entry point for the radiation and a waist point,
   wherein a distance between the entry point and the waist point is approximately equal to a distance between the entry point and the effective waist point.

12. The resonator as recited in claim 11, wherein the distance between the entry point and the waist point is an optical distance, the optical distance equal to a physical distance between the entry point and the waist point multiplied by an index of refraction of the second Brewster's angle retroreflector prism.

13. A resonator for a ring-down cavity spectroscopy cell having an optic axis, the resonator comprising:
   a first Brewster's angle retroreflector prism having:
      (a) a plurality of total internal reflection surfaces with one of the total internal reflection surfaces being a curved surface,
      (b) an apex angle of about 135° minus Brewster's angle,
      (c) a second angle of about 90°, and
      (d) a third angle of about 180° minus two times Brewster's angle;
   a second Brewster's angle retroreflector prism having a plurality of total internal reflection surfaces and being disposed in alignment with the first prism along the optic axis of the resonator; and
   means for coupling radiation into one of the first and second prisms.

14. The resonator as recited in claim 13, wherein at least one of the prisms is rotatable.

15. The resonator as recited in claim 13, wherein the prisms are one of fused silica, sapphire, diamond, calcium fluoride, and yttrium-aluminum-garnet (YAG).

16. The resonator as recited in claim 13, wherein the coupling means is one of a focusing lens and a mirror positioned at a predetermined distance from one of the first and second prisms.

17. The resonator as recited in claim 13, wherein the coupling means has a first astigmatism compensating for a second astigmatism of the resonator.

18. The resonator as recited in claim 17, wherein the coupling means is at least one of a focusing lens and a mirror positioned at a predetermined distance from one of the first and second prisms.

19. The resonator as recited in claim 18, wherein the coupling means has a positive focal length.

20. The resonator as recited in claim 17, wherein the coupling means is a mirror having a negative focal length, the radiation being incident on the surface of the mirror.

21. The resonator as recited in claim 20, wherein the mirror is tilted out of a plane determined by the optic axis of the resonator.

22. The resonator as recited in claim 13, wherein the curved surface has a spherical shape.

* * * * *